United States Patent [19]
Bombardelli et al.

[11] Patent Number: 5,635,185
[45] Date of Patent: Jun. 3, 1997

[54] EXTRACTS OF *PILIOSTIGMA THONNINGII,* THE USE THEREOF AND FORMULATIONS CONTAINING THEM

[75] Inventors: Ezio Bombardelli; Paolo Morazzoni; Giuseppe Mustich, all of Milan, Italy

[73] Assignee: Indena S.p.A., Milan, Italy

[21] Appl. No.: 274,407

[22] Filed: Jul. 13, 1994

[30] Foreign Application Priority Data

Jun. 1, 1994 [IT] Italy .................................. MI94A1135

[51] Int. Cl.$^6$ .......................... A61K 35/78; A61K 31/685
[52] U.S. Cl. .......................... 424/195.1; 514/78; 514/888; 514/896; 514/934
[58] Field of Search .......................... 424/195.1; 514/78, 514/934, 888, 896, 898

[56] References Cited

PUBLICATIONS

Chem. Abst. 120:158097t, Mar. 1994.

*Primary Examiner*—John W. Rollins
*Attorney, Agent, or Firm*—Bucknam and Archer

[57] ABSTRACT

The present invention relates to novel extracts of *Piliostigma thonningii* Schum. having antiviral action, the process for the preparation thereof, the therapeutical use thereof and formulations containing said extracts. These novel extracts are used in the treatment of pathologies of viral origin, such as herpetic, influenza and broncho-pulmonary diseases and they also proved to be active on HIV virus.

17 Claims, 1 Drawing Sheet

EXTRACTS OF *PILIOSTIGMA THONNINGII*, THE USE THEREOF AND FORMULATIONS CONTAINING THEM

*Piliostigma thonningii* Schum, a plant widespread in the African continent, is a low trunk leguminous plant typical of savannah; in Tanzania and in Zambia the root bark of this plant is boiled in milk to use in the treatment of cough; Swahilis people eat the leaves in small amounts to treat pulmonary complications and Has chew fresh leaves as a remedy against cough. Similar uses are reported in many other African countries. Again in Africa, different parts of the plant are used to cure inflamed gums and for the medication of wounds and various ulcerations.

During experimental researches to verify the pharmacological properties of the plant, it has surprisingly been found that the extracts prepared according to the invention have antiviral activity on human pathogenic viruses recently isolated from infected persons.

From the chemical point of view, little is known about the composition of the roots, branches and leaves of *Piliostigma thonningii*. Up to 20% of tannin was recovered from the branches bark, but the composition was not clarified, whereas some flavonoids and terpenes such as lambertianic acid and lambertianol were identified in the leaves.

The extracts of the present invention are prepared extracting all the parts of the plant, separately or in a mixture thereof, with aliphatic low molecular weight alcohols or ketones, pure or diluted with water. The barks of the root and trunk are mainly extracted with aqueous acetone in a concentration varying from 9:1 to 2:8, preferably 6:4, at temperatures ranging from 25° C. to 60° C., preferably at 40° C. Leaves, on the contrary, are mainly extracted with alcohols or ketones mixtures, usually with acetone, in a 4:6 solvent/water ratio, to avoid the extraction of chlorophyll and undesired lipophilic substances which proved to be inactive during the screening. The resulting extracts, as it will be illustrated in the following examples, are subjected to the following treatment steps:

a) elimination of the solvent by means of concentration at a temperature below 40° C.;

b) filtration or centrifugation to remove the gummy residues of undesired substances formed during the elimination of the organic solvent;

c) extraction of the clear aqueous extract with ethyl acetate to complete exhaustion in the extractable substances and elimination of the organic extracts;

d) chromatography of the aqueous phase on a column of an adsorption resin, such as XAD-4, XAD-2, Duolite or other polystyrene matrix resins; re-elution with aliphatic low molecular weight alcohols or ketones diluted with water, preferably with aqueous acetone in different percentages, usually with 40% aqueous acetone;

e) partial concentration of the eluate from the column under vacuum and at temperatures not above 60° C.;

f) evaporation of the concentrate to dryness under vacuum;

g) dissolution of the residue in a small volume of methanol; and h) treatment of the solution with an amount of methylene chloride sufficient to precipitate the active ingredient.

An abundant reddish precipitate is obtained, which is soluble in water and insoluble in all the aprotic solvents, having antiviral activity. This product can be used as such or further fractionated on a column of, for example, Sephadex LH 20, or on equivalent matrixes, according to the following standard: the extract dissolved in 95% ethanol is adsorbed on the matrix, eluting subsequently with the same solvent the low molecular weight undesired substances; the elution is continued with ethanol/water mixtures, preferably ranging from 30 to 60% in organic solvent or better with acetone/water mixtures ranging from 29 to 70% in organic solvent, preferably from 35 to 45%. The hydroalcohol or acetone eluates are collected in fractions which, after checking by gel permeation, are pooled according to similar molecular weights and concentrated to elimination of the solvent and freeze-dried. The fractions with molecular weights from 1500 to 2500 daltons, preferably with molecular weight of about 2100 daltons, turned out to be particularly active.

Alternatively, the aqueous solution, after extraction with ethyl acetate (see step c) above) can be extracted with n-butanol/toluene mixtures, preferably in a 9:1 ratio; the butanol extracts can subsequently be purified according to the above described procedures.

The antiviral activity was tested with conventional methods reported in literature or partly modified by the Applicant. By way of example, monkey cells (African green monkey cells (VERO) Flow Laboratories Ltd. Irvine, Scotland) are cultured in TC-199 medium containing 1% glutamine, added with calf serum (5% in the non infected cultures and 2.5% in those infected) containing or not containing the virus under test and in presence or the absence of the active substance to test.

To evaluate the extracts of the present invention, two different kinds of controls were carried out: one concerning the real antiviral activity and one on the cytotoxicity of the substances, so as to define the activity/toxicity ratio. The VERO cells were layered at $2\times10^{-4}$ on a plate; after 24 hours incubation the cell monolayers were infected with the selected virus and immediately after treated with scalar concentrations of the *Piliostigma thonningii* derivatives; 24 hours later they were evaluated through a microscope for the specific activity.

For the evaluation of cytotoxicity, the VERO cells were layered at a concentration of $1\times10^5$; 24 hours later the cells were freed from the culture medium, which in its turn was replaced by a culture medium containing different concentrations of the extracts under test. After 48 hours, the cells were fixed with 1% glutaraldehyde in Hank's solution, the plates were washed with deionized water for 15 minutes and dried in the air; the dye (Crystal Violet) adsorbed on the cells was extracted with a 0.2% solution of Triton X-100 2 and checked spectrophotometrically. The cytotoxicity was tested more easily by incubating the cells as above indicated, at a $2\times10^4$ density per well; after 24 hours the medium is removed and the cells were treated with the test substances; after 48 hours incubation the cells were added with 0.5 mCi/plate of $^3$H-thymidine. The cells were further incubated for 16 hours more under $CO_2$ atmosphere, thereafter quantitatively measuring the incorporation with a scintiller. In such a way, the $CC_{50}$ (concentration reducing by 50% the thymidine uptake compared with controls) was evaluated.

The screening of the *Piliostigma thonningii* derivatives allowed to identify substances having antiviral activity on human herpes viruses (Herpes simplex 1 and 2), on cytomegalovirus and on HSV-1 and HSV-2; moreover, the extracts proved to be active on different strains of influenza and syncytial viruses. By way of example, on herpes viruses, using the still unfractionated extract (Example I) at a concentration of 15.6 ug/ml, a 100% reduction in the formation of the plaques versus controls and a cytotoxicity of 62.5 ug/ml were obtained; the activity/cytotoxicity ratio is markedly in favour of the activity, thereby the product has a valuable therapeutical index. The $EC_{50}$ of the same product on replication of the HSV-1 and HSV-2 viruses was respectively of 22.4 and 36.2 ug/ml. The fractions of this extract, such as those reported in the Examples III and IV, evidenced a specific activity higher than the one of the starting extract, further positively increasing the activity/toxicity ratio. The $EC_{50}$ versus herpes viruses were, for example, respectively of 5.1 and 6.4 ug/ml with a cytotoxicity higher than 100 ug/ml.

On the para-influenzal virus, the extracts of the invention proved in all the tests a surprisingly high activity, thus showing to be valuable for the treatment of the most various influenza forms.

As far as the action mechanism or the certain identification of the active principles are concerned, little is known up to now. The active principles of the extracts of the present invention are partly of polyphenol nature and are likely to be active (HIV) in reducing the expression of the antigen in culture and in reducing syncyctia. In this sense, the extracts have turned out to be particularly active on the various cells models used when the product is added to the culture simultaneously with the entrance of the virus and not after the entrance took place. From these data it can be assumed that the extract or its fractions act on the first phases of the infection, even though it cannot be excluded that their activity could inhibit the enzyme action of reverse transcriptase and/or of the protease.

The extracts of the invention are active in man starting from doses of 10 mg to 5 g day, depending on the administration route as well as the severity of the disease to treat. For the treatment of herpes, the extracts and their fractions can be administered in the form of ointments or formulations for the topical use, as required for this kind of therapy, or by the oral or intravenous routes; for all of the other types of viruses, the extracts are mainly administered by the oral, intravenous or aerosol routes, merely dissolved in water or carried by conventional excipients.

According to a further object of the present invention, the oral formulations of the extracts of the invention are carried in both natural and synthetic phospholipids. Preferably the phospholipid to extract (or extract fractions) ratio varies from 1 to 3 parts by weight; the mixtures of these extracts with the phospholipids are usually/preferably administered in soft gelatin capsules, in the presence of carriers such as migliol and the like, or in hard gelatin capsules or in tablets.

The extracts of the invention can be used for the acute or chronic treatment, depending on the pathology; both the extract and its fractions cause no particularly notable toxic effects up to 5 g/kg in the rat and in the mouse, when administered orally, whereas they are tolerated up to 500 mg/kg when administered intravenously.

BRIEF DESCRIPTION OF THE DRAWING

The FIGURE shows the SEC-chromatography profile of the purified extract of the *Piliostigma thonningii* of the invention. The term SEC-chromatography means size exclusion chromatography. On the axis of the abscissa are plotted the values of the retention times of the different components of the extract eluted from the chromatographic column. On the ordinate are plotted the values of absorbance expressed in M $10^-$ volts.

The following examples illustrate the invention without limiting it.

EXAMPLE I

Figure 1:
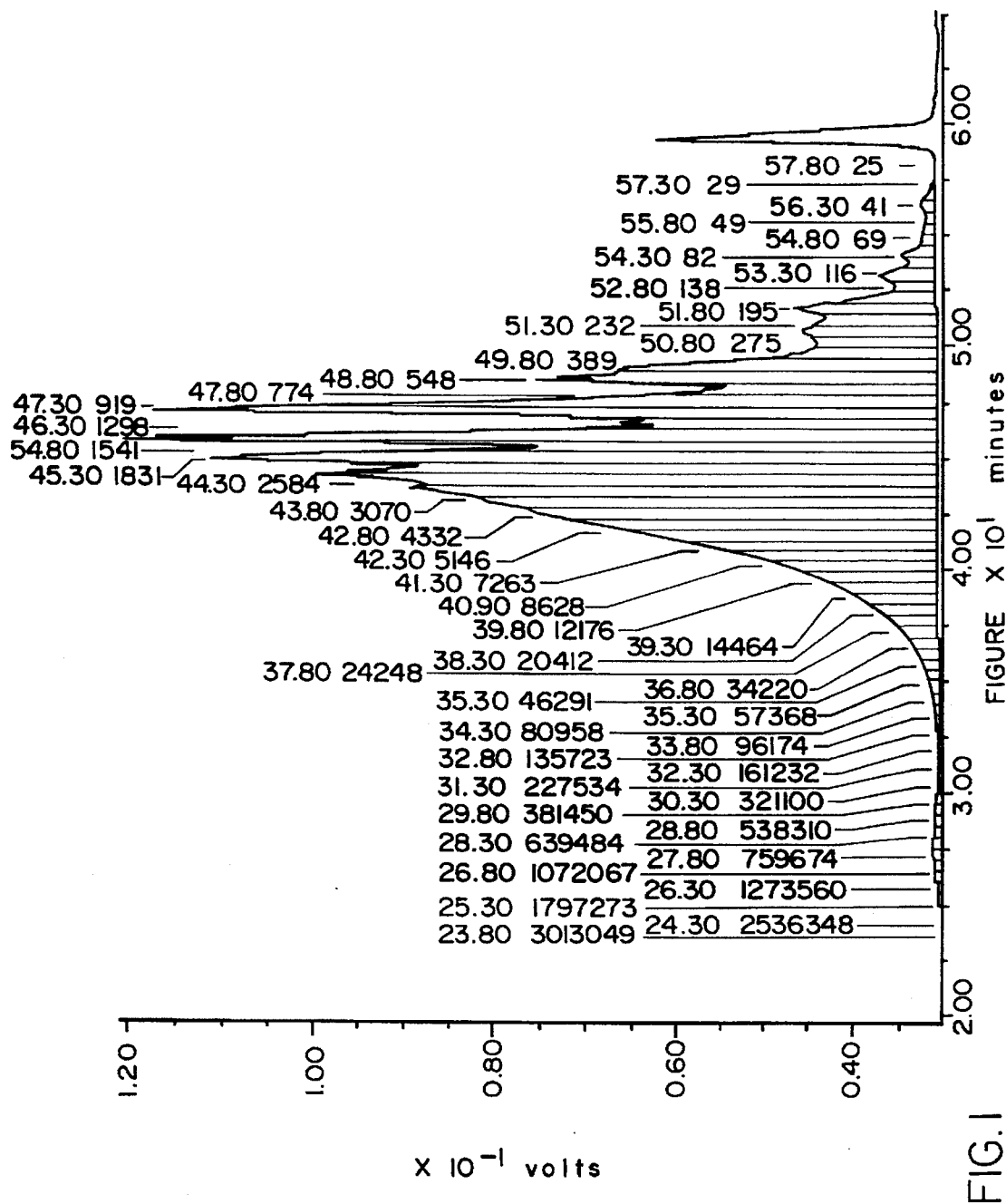

Preparation of the total purified extract from root bark of *Piliostigma thonningii*.

5 kg of finely ground root bark of *Piliostigma thonningii* are extracted at 40° C. with 10 volumes of a 60% (w/w) acetone/water mixture; extraction is carried out under stirring and it is repeated three times. The hydroacetone extracts are concentrated to complete elimination of acetone; during the concentration the water-insoluble materials precipitate and are accurately removed by centrifugation. After extraction with ethyl acetate, the clear aqueous solution is passed very slowly through a column containing 5 kg of XAD4 adsorption resin; after the extract has passed, the elution of the column is continued with demineralized water to colourless water or anyhow with a residue lower than 0.001%. Subsequently, the resin is eluted with 40% aqueous acetone. The elution is continued until colourless liquid. The eluate from the column is concentrated to 5 l at a temperature not above 40° C.; the concentrate is filtered to remove any insoluble residues and spray-dried, to obtain 250 g of dry extract which can be used as such or re-purified according to Example II. This extract has a E1% 690 at 260 nm in MeOH. The product is freely soluble in water, alcohol, acetone and insoluble in chlorinated solvents and ethers. It can be used for the treatment of diseases of viral origin.

EXAMPLE II

Purification of the extract from *Piliostigma thonningii*.

200 g of the extract from *Piliostigma thonningii* prepared according to Example I are dissolved in 1 l of anhydrous acetone and, when dissolution is complete, they are poured under strong stirring into 5 l of methylene chloride; an abundant precipitate forms which is collected by centrifugation, washed again with methylene chloride to colourless mother liquors and finally dried under vacuum at 40° C. until the solvent is completely removed. 170 g of a reddish compound are obtained, which can be used in the treatment of viral diseases.

The SEC-Chromatography of the extract has the profile reported in the accompanying FIGURE.

EXAMPLE III

Fractionation of the extract from root bark of *Piliostigma thonningii*.

20 g of the extract prepared according to Examples I or II are dissolved in 500 ml of 95% ethanol and chromatographed on a column containing 350 g of Sephadex LH20 previously equilibrated with the same solvent. After adsorption of the solution, the column is eluted with ethanol until exhaustion in the soluble substances. The ethanol eluate is discarded, whereas the column is eluted subsequently with 40% aqueous acetone. The hydroacetone solution is concentrated under vacuum to 200 ml and the concentrate is freeze-dried. 6 g of a brick-red product are obtained, having an average molecular weight of 2018 daltons, which can be used without further purifications as an antiviral agent

EXAMPLE IV

Preparation of an extract of trunk bark of *Piliostigma thonningii*.

5 kg of finely ground trunk bark of *Piliostigma thonningii* are extracted according to the procedure of Example I; the aqueous concentrate after filtration of the insoluble materials is extracted with 20 l of ethyl acetate; the organic phase is discarded whereas the aqueous one is extracted with a 95:5 n-butanol/toluene mixture to exhaustion in the substances extractable with this solvent. The combined extracts are dried over $Na_2SO_4$ and concentrated under vacuum to 1 l.

The concentrate is poured into 5 l of methylene chloride under strong stirring. The formed precipitate is thoroughly washed with methylene chloride and dried under vacuum at 40° C. 150 g of product having antiviral activity are obtained. This product can be purified further according to the procedure of Example III.

EXAMPLE V

Formulation containing an extract of *Piliostigma thonningii* for the topical use.

20 g of purified extract of *Piliostigma thonningii* prepared according to Example III are mixed with 40 g of soy phosphatidylcholine and the whole is dissolved in 600 ml of a 9:1 methylene chloride/methanol mixture; when the two products are completely dissolved, the solvent is removed under vacuum. The resulting solid is microdispersed under strong stirring in 1200 ml of deionized water. The aqueous microdispersion is gelified by addition of 1% carboxymethyl cellulose. This aqueous gel is used in the topical treatment of herpes diseases.

EXAMPLE VI

Preparation of soft gelatin capsules containing 150 mg of a purified fraction of *Piliostigma thonningii*.

20 g of purified extract of *Piliostigma thonningii* prepared according to Example III are mixed with 40 g of soy phosphatidylcholine and the whole is dissolved in 600 ml of a 9:1 methylene chloride/methanol mixture; when the two products are completely dissolved, the solvent is removed under vacuum. The resulting solid is suspended in 180 ml of migliol and filled into soft gelatin capsules in the amount of 450 mg of extract/phospholipid mixture.

We claim:

1. A process for the preparation of extracts from the plant *Piliostigma thonningii*, said plant having bark of the root, trunk and leaves, which consists of extracting the barks of the root and the trunk with aqueous acetone in a concentration varying from 9:1 to 2:8 at temperatures ranging from 25° to 60° C., or extracting the leaves with alcohols or ketones mixtures in a 4:6 solvent/water ratio or, alternatively, in extracting said barks and said leaves mixed together, then
   a) eliminating the solvent by concentration at a temperature below 40° C.;
   b) filtering or centrifuging to remove the gummy residues of undesired substances formed during the elimination of the organic solvent to obtain a clear aqueous extract;
   c) extracting the clear aqueous extract with ethyl acetate to remove the extractable substances;
   d) subjecting the aqueous phase from step c) to chromatography on an adsorption polystyrene matrix resin column, then eluting with water and then an aliphatic low molecular weight alcohol or ketone diluted with water;
   e) partially concentrating the eluate from step d) under vacuum and at temperatures not above 60° C.;
   f) evaporating the concentrate to dryness under vacuum;
   g) dissolving the residue from step f) in a small volume of methanol; and
   h) adding to the methanol solution from step g) an amount of methylene chloride sufficient to obtain a precipitate which is soluble in water and insoluble in aprotic solvents.

2. The process according to claim 1 wherein in step d) the aqueous ketone is 40% aqueous acetone.

3. Extracts from *Piliostigma thonningii* obtained according to the process of claim 1.

4. The process of purification of the precipitate obtained in claim 1, step h) which consists of
   i) dissolving said precipitate in 95% ethanol to obtain a solution;
   l) adsorbing said solution from step i) on a matrix;
   m) eluting with 95% ethanol to remove the undesired low molecular weight substances;
   n) subsequently eluting with 30–60% ethanol/water mixture or 29–70% acetone/water mixture;
   o) pooling the fractions from step n) depending on the molecular weight thereof, concentrating and freeze-drying to obtain a fraction of molecular weight ranging from 1500 to 2500 daltons.

5. The process according to claim 4 wherein in step l) the matrix is Sephadex LH 20.

6. The extract obtained by the process according to claim 4.

7. A process for the preparation of extracts the plant *Piliostigma thonningii*, said plant having bark of the root, trunk and leaves which consists of extracting the barks of the root and the trunk with aqueous acetone in a concentration varying from 9:1 to 2:8 at temperatures ranging from 25° to 60° C., or extracting the leaves with alcohols or ketones mixtures in a 4:6 solvent/water ratio or, alternatively, in extracting said barks and said leaves mixed together, then
   a) eliminating the solvent by concentration at a temperature below 40° C.;
   b) filtering or centrifuging to remove the gummy residues of undesired substances formed during the elimination of the organic solvent to obtain a clear aqueous extract;
   c) extracting the clear aqueous extract with ethyl acetate to remove the extractable substances and to obtain an aqueous phase;
   d) extracting the aqueous phase from step c) with a n-butanol/toluene mixture in a 9:1 ratio, concentrating and diluting with methylene chloride to obtain a precipitate which is soluble in water but insoluble in aprotic solvents.

8. Extracts from *Piliostigma thonningii* obtained according to the process of claim 7.

9. The process of purification of the precipitate obtained in claim 7, step d), which consists of
   i) dissolving said precipitate in 95% ethanol to obtain a solution;
   l) adsorbing said solution from step i) on a matrix;
   m) eluting with 95% ethanol to remove the undesired low molecular weight substances;
   n) subsequently eluting with 30–60% ethanol/water mixture or 29–70% acetone/water mixture;
   o) pooling the fractions from step n) depending on the molecular weight thereof, concentrating, freeze-drying to obtain a fraction of molecular weight ranging from 1500 to 2500 daltons.

10. The process according to claim 9 wherein in step l) the matrix is Sephadex LH 20.

11. The extract obtained by the process according to claim 9.

12. A pharmaceutical composition for the treatment of herpes diseases, acquired immunodeficiency connected with HIV, influenza and cold, containing as the active ingredient the extracts according to claim 4.

13. A pharmaceutical composition for the treatment of herpes diseases, acquired immunodeficiency connected with HIV, influenza and cold, containing as the active ingredient the fractions of the extracts according to claim 9.

14. A pharmaceutical composition according to claim 12 which additionally contains a carrier, said carrier being a natural or a synthetic phospholipid, wherein the ratio of said phospholipid to said active ingredient is 1 to 3 parts by weight.

15. A pharmaceutical composition according to claim 13 which additionally contains a carrier, said carrier being a natural or a synthetic phospholipid, wherein the ratio of said phospholipid to said active ingredient is 1 to 3 parts by weight.

16. The method of treatment of a human being affected by a pathology originated from human pathogenic viruses which consists of administering to said human being an effective amount of the extract from *Piliostigma thonningii* obtained according to the process of claim 4.

17. The method of treatment of a human being affected by a pathology originated from human pathogenic viruses which consists of administering to said human being an effective amount of the extract from *Piliostigma thonningii* obtained according to the process of claim 9.

* * * * *